(12) United States Patent
Stewart

(10) Patent No.: US 8,328,994 B2
(45) Date of Patent: Dec. 11, 2012

(54) ETHANOL RECOVERY SYSTEM FOR CELLULOSIC FEEDSTOCKS

(76) Inventor: David A. Stewart, Boca Raton, FL (US)

( * ) Notice: Subject to any disclaimer, the term of this patent is extended or adjusted under 35 U.S.C. 154(b) by 383 days.

(21) Appl. No.: 12/643,468

(22) Filed: Dec. 21, 2009

(65) Prior Publication Data

US 2010/0167367 A1 Jul. 1, 2010

Related U.S. Application Data

(60) Provisional application No. 61/139,217, filed on Dec. 19, 2008.

(51) Int. Cl.
*B01D 3/06* (2006.01)
*B01D 3/10* (2006.01)
*B01D 3/42* (2006.01)
*C12P 7/12* (2006.01)

(52) U.S. Cl. .................. 203/1; 203/3; 203/19; 203/88; 203/91; 203/96; 426/11; 426/494; 435/161; 435/163; 435/183; 435/813; 568/916

(58) Field of Classification Search .................. 203/1, 3, 203/19, 88, 91, 96; 435/161, 163, 183, 813, 435/814; 426/11, 494; 568/916

See application file for complete search history.

(56) References Cited

U.S. PATENT DOCUMENTS

| 4,337,123 | A | * | 6/1982 | De Sa et al. | 203/19 |
| 4,952,503 | A | * | 8/1990 | Granstedt | 435/161 |
| 4,952,504 | A | * | 8/1990 | Pavilon | 435/163 |
| 2007/0000769 | A1 | * | 1/2007 | Brown | 203/19 |
| 2009/0127092 | A1 | * | 5/2009 | Tedder | 203/19 |
| 2009/0171129 | A1 | * | 7/2009 | Evanko et al. | 568/916 |

* cited by examiner

*Primary Examiner* — Virginia Manoharan
(74) *Attorney, Agent, or Firm* — Fleit Gibbons Gutman Bongini & Bianco PL; Jon A. Gibbons

(57) ABSTRACT

Processes for the recovery of ethanol, useful as a fuel, from various cellulosic feedstock materials fermented to produce ethanol-containing beer are disclosed. The present invention provides a method and a system for ethanol recovery from highly viscous fermented citrus waste biomass. The systems overcome various challenges, including effectively stripping the ethanol from biomass beer in an energy efficient and economical manner that may allow for the further dehydration of the ethanol/water mix in a traditional rectifier distillation column. In certain embodiments, a series of flash stages and beer stripping columns are capable of operating with highly viscous slurries and/or feedstocks containing high levels of solids.

11 Claims, 2 Drawing Sheets

ETHANOL RECOVERY SYSTEM FOR CELLULOSIC FEEDSTOCKS

CROSS-REFERENCE TO RELATED APPLICATIONS

This application is based upon and claims priority from prior U.S. Provisional Patent Application No. 61/139,217, filed on Dec. 19, 2008, the entire disclosure of which is herein incorporated by reference. This Application is related to co-pending U.S. Provisional Patent Application No. 61/139,268 and U.S. Provisional Patent Application No. 61/139,360 each filed on Dec. 19, 2008, the entire disclosure of which each is herein incorporated by reference.

FIELD OF THE INVENTION

This invention relates to processes for the recovery of ethanol from various cellulosic feedstock materials that have been fermented to produce an ethanol-containing beer. More particularly, the present invention relates to processes capable of handling highly viscous slurries and/or feedstocks containing high levels of solids that may strip ethanol from biomass beer in an energy efficient manner.

BACKGROUND OF THE INVENTION

Ethanol is a major chemical used in human beverages and food, as an industrial chemical, and as a fuel or a fuel additive in reformulated gasoline that is designed to reduce emissions from automobiles. This invention relates mainly to the production of ethanol for use as a chemical or fuel.

D. Verser (U.S. Pat. Nos. 6,509,180 and 7,351,559) discloses a process for producing ethanol that includes a combination of biochemical and synthetic conversions reportedly resulting in high yield ethanol production with concurrent production of co-products.

D. W. Tedder (U.S. Pat. No. 4,517,298) discloses a method of producing alcohol which is at least substantially free of water using a combined fermentation/extraction process.

F. Shinskey (U.S. Pat. Nos. 4,358,346 and 4,502,921) discloses the control of multiple distillation columns for producing anhydrous alcohol suitable for blending with gasoline to produce gasohol.

Ethanol can be derived from carbohydrates to produce ethanol in two basic conversion steps. The first reaction is hydrolysis of the carbohydrates into fermentable sugars, sometimes referred to as saccharification. The second reaction involves the conversion of the sugars to ethanol, commonly done by fermentation with a yeast or some other fermenting micro-organism.

Ethanol produced from the carbohydrates in biomass materials is often referred to as cellulosic ethanol and is usually produced from non-food crops such as agricultural residues (e.g., citrus peel waste ("CPW"), wheat straw, corn stover, bagasse, beet pulp, apple pommace, and corn husks), woody materials (e.g., hurricane debris, sawdust, soft wood, hard wood, and forestry waste), energy crops (e.g., switch grass, canes, and poplar trees) and waste materials like Municipal Solid Waste ("MSW").

Regardless of the source, efficient utilization of sugars theoretically increases the overall yield of ethanol from biomass and makes production more economically attractive. However, a major limitation of known processes is the complexity and viscosity of the hydrolyzate that results from treatment of the biomass to produce the fermentation medium.

The basic science for converting CPW into ethanol was developed over ten years ago. CPW contains several mono and disaccharides, the main ones being glucose, sucrose and fructose. In addition, CPW contains polysaccharides such as cellulose, hemicellulose and/or pectin (Ting and Deszyck, 1961).

In order to maximize the monosaccharide levels, the polysaccharides present in the CPW may be hydrolyzed. For example, cellulose, hemicellulose and pectin are hydrolyzed using a cocktail of pectinase, cellulase, and beta-glucosidase enzymes to produce glucose, fructose, arabinose, xylose, galactose, rhamnose, and galacturonic acid (GA) (Nishio and Nagai, 1979; Marshall et al., 1985; Ben-Shalom, 1986; Echeverria et al., 1988; Grohmann and Baldwin, 1992; Grohmann et al., 1994, 1995). In turn, the monosaccharides such as fructose, glucose, sucrose, and galactose from citrus waste hydrolysates can be fermented by Saccharomyces cerevisiae yeast (typically used in the brewing industry) to produce ethanol (Grohmann et al., 1994).

Among the citrus waste that has been studied is peel waste from Valencia oranges, the main citrus crop in Florida. The dry matter content observed for peel waste from Valencia oranges is reportedly 24-27% by weight (Ting and Deszyck, 1961; Wilkins et al., 2005). Valencia peel having about 23% dry matter has been indicated to yield sugars for on a % dry matter basis (Grohmann and Baldwin, 1992; Grohmann et al., 1994, 1995) that theoretically provides ethanol in a yield of 6.6% by volume (5.2% by mass) (Grohmann et al., 1994).

Generally speaking, the commercial recovery of alcohol by distillation from fermentation beers has been in widespread operation for many years. Control systems for improving quality within reasonable efficiency limits have paralleled the growth of this industry. In the past, most of the alcohol distilled was for beverage purposes with no crucial requirement for a dehydrated end product, thereby alleviating to some extent both the energy required to distill the alcohol and the need for tight controls over the process. However, in the energy context, rising costs and a need for greater efficiency has focused attention on the need for optimization of energy intensive (endothermic) processes through the application of dynamic control strategies. For example, the production of ethanol from grain blended with gasoline forms the motor fuel "gasohol." To be effective as an alternative energy source, the process by which the ethanol is produced must minimize energy consumption so as to achieve "a net energy gain" and final stage ethanol should be essentially anhydrous.

Significantly, there are considerable differences between grain-based fermentation beers and cellulosic-based fermentation beers that may affect the "net energy gain." As a threshold matter, ethanol concentration in the biomass (cellulosic) brews tends to be relatively lower. Moreover, cellulosic fermentation mixtures typically have higher solids levels and/or higher viscosity than their grain-based cousins. Consequently, typical distillation trains that effectively remove ethanol from grain fermentation broths are incapable of handling the higher solids levels and/or increased viscosity present in fermented biomass mixtures. While dilution of the fermentation beer might reduce viscosity or solids related issues, it would further dilute the ethanol concentration. Diluting the beer so as to have the physical characteristics suitable for a traditional beer stripper would result in an ethanol concentration which may be too dilute for economical purification, which reportedly requires an incoming ethanol concentration of at least 3% (Alcohol Textbook 2001)

Accordingly, there is considerable interest in developing new methods for the production of ethanol from biomass that are capable of handling typical viscosities and/or solids levels associated with these feedstocks. There is also interest in developing new methods for the production of ethanol from biomass capable of separating ethanol from ethanol-containing fermented biomass mixtures efficiently and economically, and in some cases without resorting to feedstock dilution to circumvent higher viscosity and/or solids levels. The present invention is directed to these and other important ends.

SUMMARY OF THE INVENTION

Accordingly, it is an object of the present invention to provide methods for producing ethanol.

It is another object of the present invention to provide improved ethanol separation from biomass.

It is another object of the present invention to provide methods for recovering ethanol that overcome high viscosity and/or high solids levels.

It is another object of the present invention to provide methods for effectively stripping the ethanol from viscous and/or high solids fermentation beers in an energy efficient and economical manner.

It is another object of the present invention to provide methods for simplifying the ethanol process train.

It is another object of the present invention to provide methods for dehydrating an ethanol/water mix can be performed in a traditional rectifier distillation column.

It is another object of the present invention to provide methods for treating the whole stillage.

These and other objects will become apparent in the brief description of the drawings and the detailed description of the illustrative embodiments.

DETAILED DESCRIPTION OF ILLUSTRATIVE EMBODIMENTS

Figure 1:
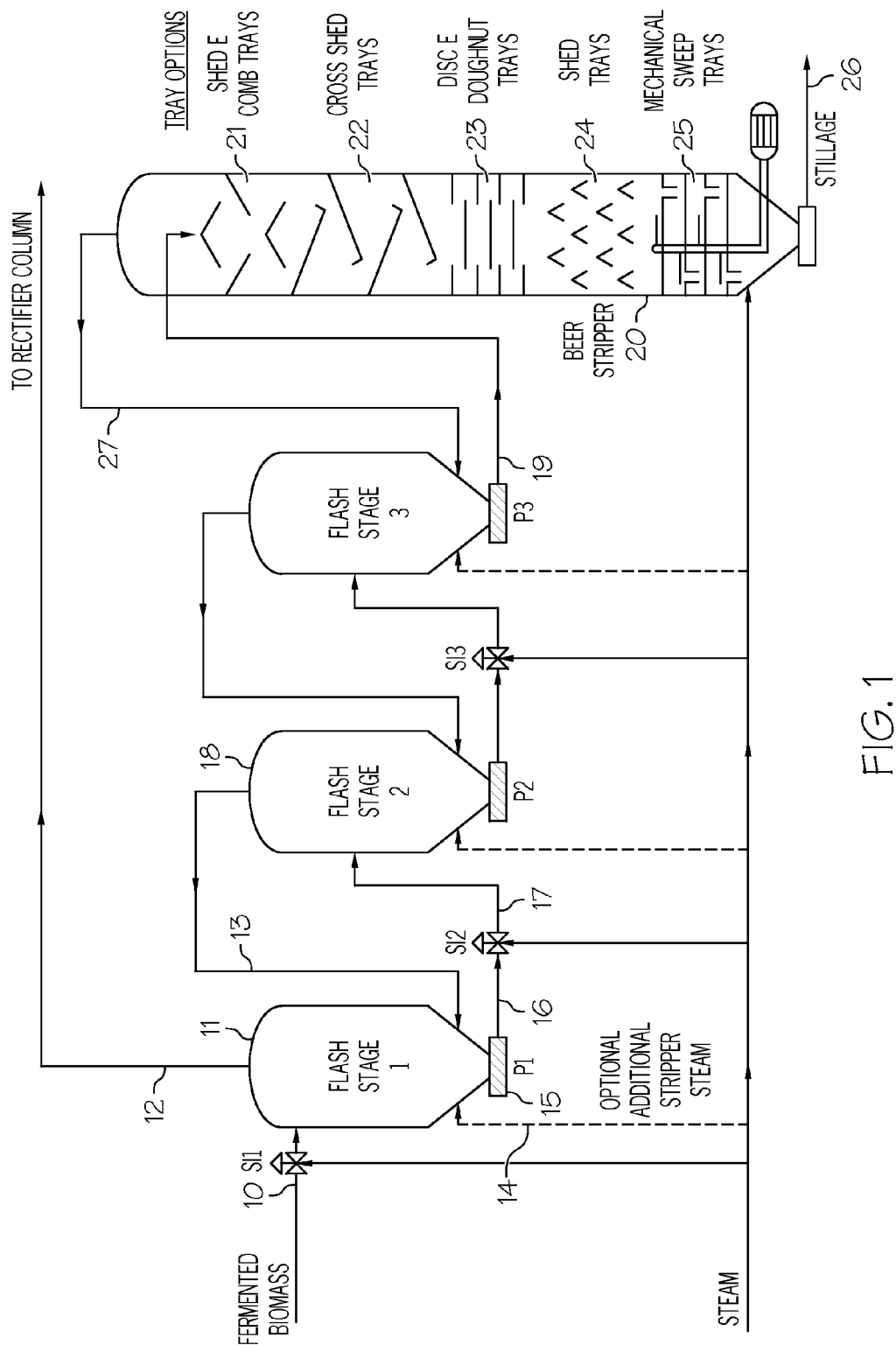
FIG. 1 is a simplified flow schematic diagram of an ethanol from biomass production plant of the present invention employing a countercurrent design.

The present invention is generally directed to processes for the recovery of ethanol from various cellulosic feedstock materials fermented to produce ethanol-containing beer. More particularly, the present invention relates to processes capable of handling highly viscous slurries and/or feedstocks containing high levels of solids that may effectively strip ethanol from biomass beer in an energy efficient and economical manner.

The advantages of the methods of the present invention include without limitation improved ethanol separation from biomass. In certain embodiments, ethanol may be separated without excessive dilution with water to overcome issues associated with high viscosity and/or high solids levels. The ability of the improved methods to overcome the challenge of effectively stripping the ethanol from viscous and/or high solids fermentation beers allows for simplification in the overall process train. For example, in certain embodiments, subsequent dehydration of the ethanol/water mix can be performed in a traditional rectifier distillation column. Further, the remaining whole stillage, which is typically dewatered into either animal feed or fuel for boiler systems, is preferably not excessively diluted in the present system. Under such circumstances, any dewatering energy and financial costs are minimized.

As employed above and throughout the disclosure, the following terms, unless otherwise indicated, shall be understood to have the meanings below with the understanding that the examples provided in the definitions include but are not limited to the recited examples.

As used herein, the terms "citrus" or "citrus fruit" includes all citrus fruits commercially available, including those in commercial production such as oranges, grapefruits, etc.

As used herein, the terms "citrus peel waste," "citrus waste," "citrus waste solids," or "CPW" includes the citrus peel, segment membranes (pulp) and/or seeds.

As used herein, the term "biomass" refers to any renewable organic material used for the production of alternative fuels (such as ethanol) typically for its cellulose content rather than its starch or sugar content. Examples of biomass include, without limitation, citrus waste, wheat straw, corn stover, corn husks, rice straw, bagasse, beet pulp, pommace, woody materials (e.g., hurricane debris, sawdust, soft wood, hard wood, and forestry waste), energy crops (e.g., switch grass, canes, and poplar trees) and Municipal Solid Waste ("MSW"), whether used alone or in any combination. Such combinations include mixtures of biomass and crops typically of interest in ethanol fermentation primarily for their starch and/or sugar content, so long as the majority of fermentable sugars comes from biomass materials as defined herein. Crops such as potatoes, wheat, rye, triticale, corn, barley, sorghum and manioc and sugar cane juice, molasses, and beet sugars and the like are typically of interest in ethanol fermentation primarily for their starch and/or sugar content.

As used herein, the term "beer" refers to any ethanol containing mixture created by fermenting biomass, wherein biomass is as defined hereinabove.

As used herein, the term "stillage" refers to the residue at the bottom of a still after fermentation, containing solids but less alcohol compared to the beer prior to its distillation.

As used herein, the term "supernatant" refers to any liquid and/or solid liquid composition that is provided when a mechanical separator means is employed to separate at least some of the solids from a solids-containing liquid material. Under such circumstances, the supernatant has a lower solids content than the original solids-containing liquid material. Supernatant therefore includes without limitation decantates from the sedimentation processes, supernatants from centrifugation processes, filtrates from filtrations, etc. Preferably, the remaining solids are either substantially soluble or absent in the supernatant.

As used herein, the term "substantially soluble" means that more than about 50% by weight of the solids contained in a supernatant are soluble. Preferably, more than about 75% are soluble. More preferably, more than about 90% are soluble. Even more preferably, more than about 95% are soluble. Most preferably, more than about 99% are soluble.

As used herein, reference to solids in the original solids-containing liquid material being "substantially absent" from the supernatant means that less than about 20% by weight are present, preferably less than about 15%, more preferably less than about 10%, even more preferably less than about 5% and most preferably less than about 1%.

When ranges are used herein for physical properties, such as molecular weight, chemical properties or chemical formulae, all combinations and sub-combinations of ranges and specific embodiments therein are intended to be included.

The disclosures of each patent, patent application and publication cited or described herein are hereby incorporated by reference, in their entirety.

When any variable occurs more than one time in any constituent or in any process, its definition in each occurrence is independent of its definition at every other occurrence. Combinations of variables are permissible only if such combinations result in viable processes. When ranges are used for physical properties of components, or reaction conditions, such as weight percent, content, viscosity, temperatures, pressures, etc., all combinations and sub-combinations of ranges and specific embodiments therein are intended to be included.

It is believed that the names, characterizations, description, etc. used herein correctly and accurately reflect the chemicals, systems and methods. However, the nature and value of the present invention does not depend upon the theoretical correctness of these, in whole or in part. Thus, it is understood that the nomenclature is not intended to limit the invention in any way.

The present invention is directed, in part, to new processes for the separation of ethanol from ethanol-containing fermented biomass mixtures, preferably wherein the biomass is a form of citrus waste.

In a first embodiment, the present invention provides processes for the preparation of ethanol from a fermented biomass mixture, comprising:
(a) separating an ethanol-containing fermented biomass mixture into:
  (1) an overhead aqueous ethanol stream containing at least part of the ethanol from the ethanol-containing fermented biomass mixture; and
  (2) a bottoms stream containing a reduced-ethanol content biomass mixture;
(b) optionally repeating step (a) using the bottoms stream as the ethanol-containing fermented biomass mixture;
(c) feeding the remaining bottoms stream into a distillation column to remove as an overhead aqueous ethanol distillation stream at least a portion of the ethanol entrained in the bottoms stream; and
(d) dehydrating the one or more overhead aqueous ethanol streams in a distillation column to provide ethanol;
wherein the initial ethanol-containing fermented biomass mixture has a viscosity of at least about 500 cP.

In certain embodiments, the present invention provides processes for the preparation of ethanol from a fermented biomass mixture, comprising:
(a) providing an ethanol-containing biomass mixture;
(b) optionally heating the ethanol-containing biomass mixture;
(c) separating the ethanol-containing fermented biomass mixture into:
  (1) a supernatant having a reduced solids content relative to the ethanol-containing fermented biomass mixture; and
  (2) a solids portion;
to remove at least a portion of the solids contained in the ethanol-containing biomass mixture;
(d) optionally separating the supernatant into:
  (1) an overhead aqueous ethanol stream containing at least part of the ethanol from the supernatant; and
  (2) a bottoms stream;
(e) optionally repeating step (d) using the bottoms stream as the supernatant;
(f) feeding the supernatant from step (c) or remaining bottoms stream into a distillation column to remove as an overhead aqueous ethanol distillation stream at least a portion of the ethanol entrained in the supernatant from step (c) or bottoms stream; and
(g) dehydrating the one or more overhead aqueous ethanol streams in a distillation column to provide ethanol;
wherein the initial ethanol-containing fermented biomass mixture has a viscosity of at least about 500 cP.

In certain embodiments, one or more overhead aqueous ethanol streams feed to a distillation column. The column is employed to rectify the overhead aqueous ethanol stream (or combined streams) that has (have) a combined initial ethanol concentration of at least about 20% by weight of the stream or combined streams.

In certain embodiments, the methods of the present invention provide processes wherein the ethanol-containing biomass mixture is derived from a biomass feedstock comprising citrus waste.

In certain embodiments, the methods of the present invention provide processes wherein the initial ethanol-containing biomass mixture has a viscosity of from about 500 to about 20000 cP, preferably from about 1000 to about 10000 cP.

In certain embodiments, the methods of the present invention provide processes wherein a solid-liquid separation pre-treatment step is performed on the initial ethanol-containing biomass mixture to remove at least a portion of the solids contained therein, prior to the ethanol-containing biomass mixture's separation into (1) an overhead aqueous ethanol stream containing at least part of the ethanol and (2) a bottoms stream.

In certain embodiments, the methods of the present invention provide processes in which the separation of ethanol uses an extraction train containing multiple individual stages where streams can be contacted and brought to near equilibrium conditions.

In certain embodiments, the methods of the present invention minimize energy use within the process, so as to greatly reduce the ethanol recovery cost and/or accomplish this without the need for expensive and/or burdensome membrane separation techniques.

In certain embodiments, the methods of the present invention produce an ethanol rich stream which forms the feed for a traditional rectifier distillation column and which stream contains an ethanol concentration of at least twenty percent by weight.

In certain embodiments, the methods of the present invention achieve a continuous beer stripping process which is commercially practical with differing and varying biomass feedstocks.

In certain embodiments, the methods of the present invention involve reactions take all take place in vessels which are practical in construction and readily cleanable to prevent unwanted contamination by microorganisms.

In certain embodiments, the methods of the present invention involve a partial solid liquid separation using a centrifuge, mechanical press, or equivalent, prior to feeding the flash vaporization units to allow flexibility in processing beer from multiple sources of biomass.

In certain embodiments, the methods of the present invention vacuum systems are utilized to enhance beer stripping efficiency. These systems may be useful at one or more flash vaporization stages, the beer stripper stage, or both.

In certain embodiments, the methods of the present invention provide a high-quality liquid motor fuel which may be used in conventional engines, either alone or by mixing it with gasoline in any proportion.

In certain embodiments, the initial stages of the methods of the present invention involve flash vaporization units, where a single feed stream of ethanol containing fermented mixture enters a vessel, commonly called a flash drum, and is separated into two streams, more preferably, wherein the feed stream is allowed to approach vapor/liquid equilibrium in the flash vaporization unit, forming two phases.

In certain embodiments, the flash vaporization is accomplished through the use of a valve to throttle the inlet stream and lower the pressure on the feed stream just as it enters the flash drum. The efficiency of the flash vaporization units may preferably be further enhanced by the addition of stripping steam to the bottom of the unit. The two phases separated by the flash vaporization preferably exit the flash drum as an overhead ethanol-containing product and a bottoms product (reduced ethanol containing biomass mixture).

In certain embodiments, the bottoms product is fed into another separation stage, preferably a flash vaporization unit, to recover additional ethanol as an overhead stream from the bottoms product. The further processed bottoms product may be liquid, or a liquid and solid combined product. The overhead aqueous ethanol-containing product may be combined with the first overhead aqueous ethanol-containing stream and distilled together to provide an ethanol product suitable for use in fuel. At some point, preferably determined by the operator or a logic control sequence, the economics may dictate that removal of any residual ethanol by flash vaporization from the remaining bottoms product is no longer cost effective. At such time the remaining bottoms product may either be processed into cattle feed using methods known in the art or may be subjected to a beer stripping column utilizing trays capable of handling high solids and/or high viscosity materials.

The efficiency of the beer stripping column may be relatively low due to the high solids and/or high viscosity of the beer, however, the majority of the ethanol is typically recovered in the flash vaporization unit(s), which mitigates the reduced efficiency of the beer stripper.

To improve separation and stripping, multiple stages are preferably used. An even more preferred arrangement is to have countercurrent flow through the series of stages wherein the stripping steam for one stage is provided by the overhead product from the previous stage. An advantage of this arrangement is reduced steam usage and, as a consequence, reduced energy consumption. Another advantage of this design is that in the countercurrent configuration the relatively low thermal efficiency of the beer stripper is mitigated.

In certain embodiments using multiple flash vaporization stages, the requirement for the beer stripper may be altogether avoided.

In certain embodiments, the system may utilize a centrifuge, mechanical press, filter, or equivalent to achieve a partial solid liquid separation, prior to the flash vaporization stages. The effect of this separation is somewhat dependent on the characteristics of the biomass beer. When a separation of this type is employed, the supernatant passes to a later stage in the separation train. In certain embodiments, the supernatant is inputted directly to the beer stripper column.

A simplified flow schematic is shown in FIG. 1. FIG. 1 is not meant to limit the invention in any way, but rather, is being used to illustrate certain aspects of the process. Beer resulting from the fermentation of biomass feedstocks such as citrus waste, wheat straw, corn stover, corn husks, bagasse, beet pulp, pommace, woody materials, energy crops and Municipal Solid Waste may be used alone or in any combination to provide the ethanol-containing fermented biomass feedstock used in the process of FIG. 1 or other processes of the present invention.

The operation of the system shown in FIG. 1 is particularly advantageous where the feedstock has a high solids content and/or high viscosity. In general, the level of solids and/or viscosity that the system can efficiently handle is determined by pump selection. For example, current generation positive displacement pumps with auger feeds can operate with up to 40% dry solids content and viscosities up to 1,000,000 cP.

The beer may be pre-heated prior to steam being directly injected into the biomass mixture stream by steam injector 10. The method of steam injection may vary, but with the most viscous materials, a hydro-heater or jet cooker with minimal restrictions is preferably used, more preferably a type of direct steam injector that is the full bore of the input pipe with only a narrow steam diffuser in the flow of the material. The steam delivered is typically at about 50 to about 150 psi steam pressure.

The heated beer then enters the first flash stage tank 11 via a valve to designed preferably to throttle the inlet stream and/or suddenly lower the pressure on the feed stream just as it enters the flash drum. The temperature of the beer prior to the throttle, or back pressure valve will normally be in the range of about 180° F. to about 215° F. and more typically in the range of about 200° F. to about 210° F. By manipulation of process conditions known to one of ordinary skill in the art, the beer is allowed to approach vapor/liquid equilibrium, forming two phases. A baffle arrangement may preferably be used to prevent beer in the liquid/solid phase from being drawn into, or splashed into, vapor stream 12. The temperature of the ethanol/water vapor phase 12 will be in the range of about 180° F. to about 215° F., and more typically in the range of about 200° F. to about 210° F., provided that the vessel pressure is maintained at about atmospheric pressure (preferably less than about 10 psi and more preferably less than about 4 psi). Lower pressures and associated lower temperatures in all the vessels shown will necessarily result in a balanced process train if the rectifier column is being operated under vacuum.

In processes using countercurrent design, stripper steam 13 is provided from the subsequent stage 18, or from 14 in the parallel case. In some processes it is advantageous to supply stripper steam from both 14 and 18. Pump P1 15 is maintained at a flow rate which keeps the beer at an appropriate level for both the flash and strip operations, typically below half full. Generally speaking, the level in the tank should provide head space to allow the equilibrium stage to form efficiently, therefore a large volume with the lowest possible increase in pressure. For the flash, a close to empty tank is preferred. For the stripping effect the steam will preferably pass through as much material as possible. For the stripping, a close to full tank is preferable. In practice a good compromise is to have the tank about one third full.

Pump speed for P1 15 may be preferably controlled via a differential level transmitter and voltage controlled motor (VCM) or equivalent control circuit. Additional steam is preferably injected via SV2 17 into the output beer 16 before it enters the next stage flash vessel 18. The flash and strip combination is preferably repeated in as many subsequent stages as necessary to recover the required ethanol. The solid/liquid phase (partially stripped beer) output of the final flash and strip stage 19 may be at a low enough base loss (ethanol content) so as not to require further ethanol stripping from the bottoms product, but in this schematic it moves on to a beer stripper 20.

Beer 19 entering the beer stripper 20 is dispersed above the trays preferably using a dispersion device or a distribution box suitable for the material. The beer cascades down through the trays which are preferably designed to maximize vapor contact. Examples of such tray options are shown on the schematic and include "shed and cone" 21, "cross shed" 22, "disc and doughnut" 23, "shed" 24, and "mechanical sweep trays" 25. There are other options for high viscosity/high solids beer stripping trays known to the skilled artisan. Analysis of the particular conditions typically dictates the most economical tray type or combination of tray types for the particular biomass beer application. Normal determining factors preferably strike a balance between maintenance and capital costs as against ethanol recovery efficiency. For example, the "mechanical sweep trays" 25 are expected to have the greatest ethanol recovery but also the highest maintenance and capital cost. In comparison, the large one piece trays like the "cross shed trays" 22 are expected to have lower efficiency and lower costs.

It is important to note that the economics of cellulosic ethanol production differ markedly from traditional corn ethanol production. In corn-based processes, the largest material cost of producing a gallon of ethanol is the cost of the corn feedstock which is typically more than about 50% of the sales price of that gallon of ethanol. In cellulosic ethanol production processes, particularly those wherein the feedstock is an agricultural residue, the cost of the feedstock to produce a gallon of ethanol is a much smaller percentage of the sales price.

This difference impacts the amount of acceptable base loss (ethanol in the stillage) that is economically acceptable to the producer. A typical corn ethanol plant will typically seek a base loss to be below 0.02%. However, a cellulosic ethanol plant may find that the relatively low cost of the feedstock combined with the increased difficulty of ethanol recovery from high solid content/viscous beer may make the acceptable economical base loss level much higher. Accordingly, in some preferred embodiments of the present invention comprising a citrus waste feedstock, a base loss of 0.4% or lower may be economically acceptable.

The stillage 26 exits the beer stripper 20 and may either be processed for additional ethanol recovery or more normally may be further processed to recover other valuable by-products, to make animal feed, or to make boiler fuel.

The ethanol/water vapor 27 is sent either directly to a rectifier stage, or in the countercurrent case shown, is fed back through the flash and strip stages to increase ethanol concentration and reduce steam usage. In FIG. 1, the ethanol/water stream 27 exits the first flash and strip stage 11 as stream 12 which is sent to a rectifier column or other ethanol concentration device.

Figure 2:
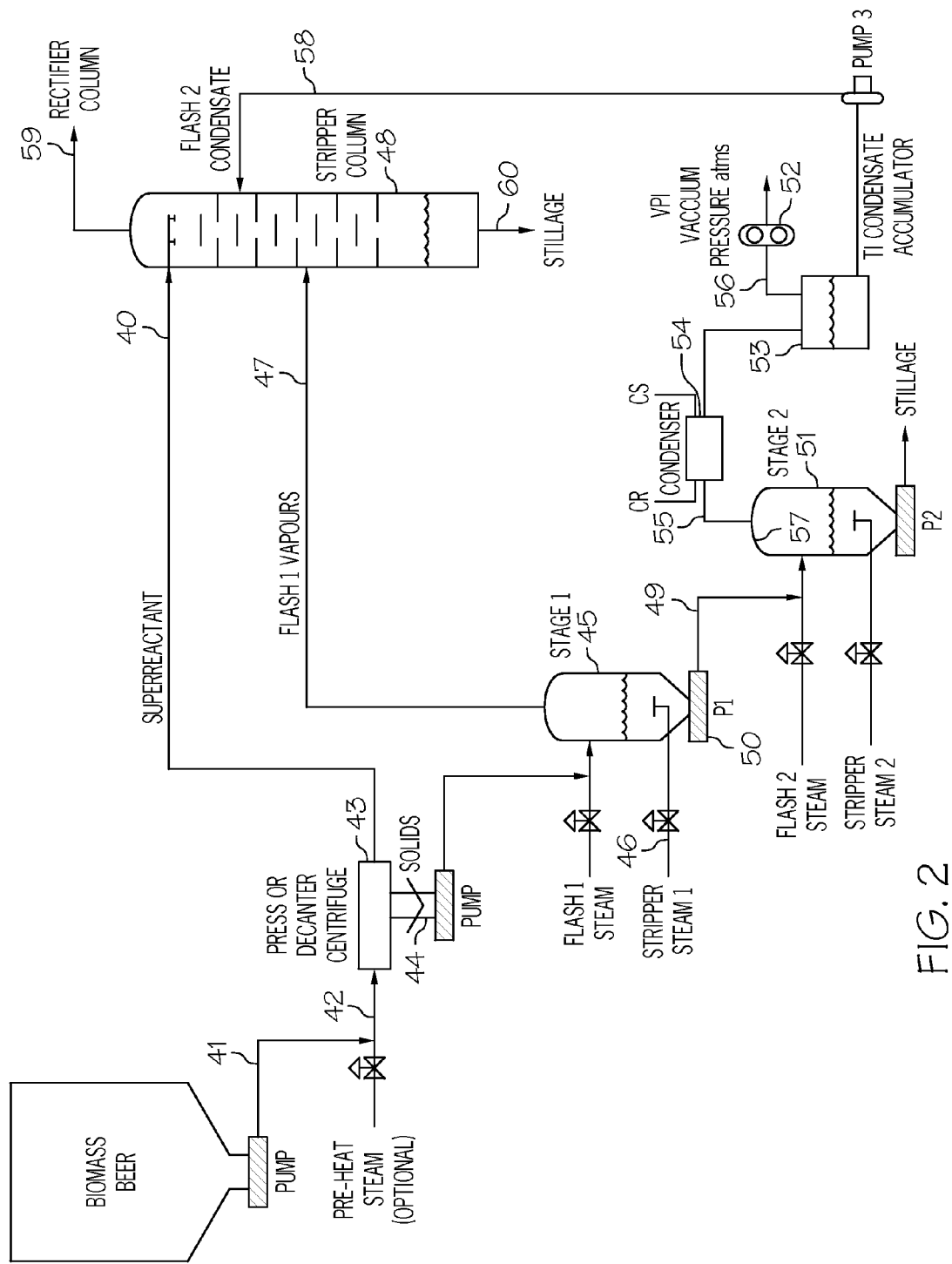
FIG. 2 is a simplified flow schematic diagram of an ethanol from biomass production plant of the present invention having a liquid solids separator prior to a flash vaporization unit.

FIG. 2 shows a system utilizing variations of the scheme used in FIG. 1. The beer 41 is optionally pre-heated with steam 42, or by use of a heat exchanger, suitable for the particular beer. An example of a suitable heat exchanger for citrus waste is a spiral heat exchanger. The optionally preheated beer enters a mechanical separator or other liquid solids separator such as a centrifuge, mechanical press, or filter system, 43 to partially separate the solid liquid stream. In a preferred embodiment, a decanter centrifuge produces a solids stream 44 with dry matter content up to the limit of the pumping system. For example, up to about 40% by weight of the solids stream, and a supernatant stream 40, may be low enough in solids content/viscosity to go directly to the beer stripping column 48. With respect to viscosity, 500 cP is the preferred maximum cP for standard columns.

The potential benefit of the decanter centrifuge, or equivalent, such as another mechanical separator or other liquid solids separator, may be assessed using the physical and chemical properties of the biomass beer. In a case where a significant percentage of the beer volume can go directly to the beer stripper then the capital, operating, and maintenance cost of the decanter centrifuge, or equivalent, may be more than offset by reduced flash and strip costs.

Solids stream 44 is pumped to flash and strip stage 45, where the process as described with reference to FIG. 1 flash and strip stage 11 is repeated. Similarly, the stripping steam 46 may be direct, or from a countercurrent source, as disclosed herein. In a variation of FIG. 1, the ethanol/water stream 47 is input directly to the beer stripper column 48. The liquid/solid stream 49 is then pumped by P1 50 to the next flash and strip stage. In this case the second flash and strip stage 51 is operated under vacuum to increase the efficiency of the phase separation. In this example the vacuum pump VP1 52 pulls a vacuum on the condensate accumulator tank T1 53 which receives the condensed ethanol/water mix from condenser C1 54. Condenser C1 54 should be sized to condense all the condensables in the ethanol/water vapor stream 55. This may result in vacuum pump VP1 52 being sized to handle the relatively small volume of non-condensables 56.

The flash and strip stages shown in FIG. 2 preferably have a simplistic baffle 57 as shown. The baffle 57 and inlet are designed to allow the feedstock to approach vapor/liquid equilibrium in the flash and/or strip stages while minimizing the quantity of solids and liquids being drawn into vapor stream 55. The flash inlet may also preferably include a dispersion device more preferably a type that is tangential or directive in nature to maximize efficiency. The stripper steam 46 is preferably added via a dispersion or mixing head.

The beer stripper column 48 has three inputs: liquid stream 40 from the partial liquid/solid separator 43; condensate stream 58 from the condensed vapor stream of a flash and strip stage; and vapor stream 47 from a flash and strip stage. The relative temperature and ethanol content of these three streams defines at what level they are each most appropriately introduced into the beer stripper 48 column. In the illustrated example, the temperature of liquid stream 40 is in the range of from about ambient to about 200° F. and enters the top of the column via a dispersion device or distributor box. Condensate 58 enters the column at a lower level than 40 based on the assumption that it is at a higher temperature than stream 40. In this example, vapor stream 47 enters the column at the lowest level of the three inputs as it is anticipated to be at the highest temperature, in relative terms to the other streams, for example at from about 200° F. to about 210° F.

As the beer cascades down the trays in stripper 48 the ethanol concentration in the liquid phase lowers as the liquid phase moves downward towards the bottom. Conversely, the concentration of ethanol increases in the vapor phase as it moves upward through the column. The output vapor phase 59 then moves to a concentration device such as a rectification column and is purified for ultimate use as fuel ethanol. The stillage 60 exits the beer stripper 48 and may either be processed for additional ethanol recovery or more normally be further processed to recover valuable by-products, such as animal feed, or boiler fuel.

Other features of the invention will become apparent in the course of the following exemplary embodiments that are given for illustration of the invention and are not to be construed as limiting the appended claims.

EXAMPLES

Example 1

An ethanol recovery system as shown in FIG. 1 designed to recover an ethanol/water stream as part of a citrus waste to ethanol plant producing 4 million gallons of denatured fuel ethanol per 7 month fruit season.

Referring to FIG. 1, the fermented citrus waste biomass 10 is hydrolyzed with enzymes and fermented to give an ethanol content of 5% by volume. The pre-heated beer has a viscosity of approximately 10,000 cP and a solids content of approximately 12%. It is envisaged to pre-heat with a 200 Proof Condenser (i.e., the thermal energy in the alcohol stream after the molecular sieves). The use of shed trays may be preferable. The beer feed rate is approximately 146,000 lbs/hr. The total steam used is approximately 25,000 lbs/hr and other than thermal losses, the thermal energy is available for use or capture by later stages. The majority of the energy is in the ethanol/water vapor stream 12 and is utilized in the rectifier column, the remainder is in the stillage output 26, which will be at approximately 200° F. and may be recovered using a spiral heat exchanger, or its equivalent. In this example, the base loss (ethanol in the stillage) is a relatively high 0.4% by weight or 0.5% by volume. Therefore, this example is designed to only recover 90% of the available ethanol. The ethanol/water stream 12 recovered in this example comprises approximately 18,000 lbs/hr of steam and 6,000 lbs/hr of ethanol vapor and thus provides an ethanol/water stream 12 of approximately 64 proof, or 32% ethanol by volume, suitable for rectification to 190 proof, or 95% ethanol.

Embodiment 1

A process for the preparation of ethanol from a fermented biomass mixture, comprising:
(a) separating an ethanol-containing fermented biomass mixture into:
  (1) an overhead aqueous ethanol stream containing at least part of the ethanol from the ethanol-containing fermented biomass mixture; and
  (2) a bottoms stream containing a reduced-ethanol content biomass mixture;
(b) optionally repeating step (a) using the bottoms stream as the ethanol-containing fermented biomass mixture;
(c) feeding the remaining bottoms stream into a distillation column to remove as an overhead aqueous ethanol distillation stream at least a portion of the ethanol entrained in the bottoms stream; and
(d) dehydrating the one or more overhead aqueous ethanol streams in a distillation column to provide ethanol;
wherein the initial ethanol-containing fermented biomass mixture has a viscosity of at least about 500 cP.

Embodiment 2

A process for the preparation of ethanol from a fermented biomass mixture, comprising:
(a) providing an ethanol-containing biomass mixture;
(b) optionally heating the ethanol-containing biomass mixture;
(c) separating the ethanol-containing fermented biomass mixture into:
  (1) a supernatant having a reduced solids content relative to the ethanol-containing fermented biomass mixture; and
  (2) a solids portion;
to remove at least a portion of the solids contained in the ethanol-containing biomass mixture;
(d) optionally separating the supernatant into:
  (1) an overhead aqueous ethanol stream containing at least part of the ethanol from the supernatant; and
  (2) a bottoms stream;
(e) optionally repeating step (d) using the bottoms stream as the supernatant;
(f) feeding the supernatant from step (c) or remaining bottoms stream into a distillation column to remove as an overhead aqueous ethanol distillation stream at least a portion of the ethanol entrained in the supernatant from step (c) or bottoms stream; and
(g) dehydrating the one or more overhead aqueous ethanol streams in a distillation column to provide ethanol;
wherein the initial ethanol-containing fermented biomass mixture has a viscosity of at least about 500 cP.

Embodiment 3

The process according to Embodiment 1 or 2, wherein the one or more overhead aqueous ethanol streams fed to the distillation column in step (d) have a combined initial ethanol concentration of at least about 20% by weight of the combined streams.

Embodiment 4

The process according to Embodiment 2, wherein the one or more overhead aqueous ethanol streams fed to the distillation column in step (g) have a combined initial ethanol concentration of at least about 20% by weight of the combined streams.

Embodiment 5

The process according to Embodiment 1, 2, 3, or 4, wherein ethanol-containing biomass mixture is derived from an initial biomass feedstock comprising citrus waste.

Embodiment 6

The process according to Embodiment 1, 3, or 5, wherein a solid-liquid separation pretreatment step is performed on the initial ethanol-containing biomass mixture to remove at least a portion of the solids contained therein prior to the ethanol-containing biomass mixture's separation in step (a).

Embodiment 7

The process according to Embodiment 1, 2, 3, 4, 5, or 6, wherein the initial ethanol-containing biomass mixture is heated prior to the solid-liquid separation.

Embodiment 8

The process according to Embodiment 1, 3, 5, 6, or 7, wherein step (a) is carried out in a flash vaporization unit.

Embodiment 9

The process according to Embodiment 2, 4, 5, or 7, wherein step (d) is carried out in a flash vaporization unit.

Embodiment 10

The process according to Embodiment 8 or 9, wherein steam is introduced into the vaporization unit to assist in the stripping of ethanol.

Embodiment 11

The process according to Embodiment 1, 3, 5, 6, 7, 8, or 10, wherein the overhead stream from step (b) or (c) is utilized as the steam for a previous separation stage.

Embodiment 12

The process according to Embodiment 2, 4, 5, 7, 9, or 10, wherein the overhead stream from step (e) or (f) is utilized as the steam for a previous separation stage.

Embodiment 13

The process according to Embodiment 3, 5, 6, 7, 8, 10, or 11, wherein a vacuum system is employed to assist the separation of ethanol in at least one of steps (a), (b), and (c).

Embodiment 14

The process according to Embodiment 3, 5, 6, 7, 8, 10, or 11, wherein a vacuum system is employed to assist the separation of ethanol in at least one of steps (d), (e), and (f).

Embodiment 15

The process according to Embodiment 1, 2, 3, 4, 5, 6, 7, 8, 9, 10, 11, 12, or 13, wherein the initial ethanol-containing biomass mixture has a viscosity of from about 500 to about 20000 cP.

Embodiment 16

The process according to Embodiment 15, wherein the initial ethanol-containing biomass mixture has a viscosity of from about 1000 to about 10000 cP.

Embodiment 17

The process according to Embodiment 1, 3, 5, 6, 7, 8, 10, 11, 13, 15, or 16, wherein the distillation column in step (c) is a stripping column packed with distillation trays capable of handling high-solids or high-viscosity feeds.

Embodiment 18

The process according to Embodiment 3, 4, 6, 7, 9, 11, 12, 13, 14, 16, 17, or 18, wherein the distillation column in step (f) is a stripping column packed with distillation trays capable of handling high-solids or high-viscosity feeds.

Embodiment 19

The process according to Embodiment 1, 3, 5, 6, 7, 8, 10, 11, 13, 15, 16, or 17, wherein the process is as described in FIG. 1.

Embodiment 20

The process according to Embodiment 2, 4, 5, 7, 9, 10, 11, 12, 14, 15, 16, or 18, wherein the process is as described in FIG. 2.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A process for a preparation of ethanol from a fermented biomass mixture, comprising:
   (a) providing an ethanol-containing biomass mixture;
   (b) separating the ethanol-containing biomass mixture into:
      (1) a supernatant having a reduced solids content relative to the ethanol-containing biomass mixture; and
      (2) a solids portion;
   to remove at least a portion of the solids contained in the ethanol-containing biomass mixture;
   (c) separating the supernatant into:
      (1) an overhead aqueous ethanol stream containing at least part ethanol from the supernatant; and
      (2) one or more bottom streams;
   (d) repeating step (c) using the bottom streams as the supernatant;
   (e) feeding the supernatant from step (b) or bottom streams remaining into a distillation column to remove as the overhead aqueous ethanol stream at least a portion of the ethanol entrained in the supernatant from step (b) or the bottom streams; and
   (f) dehydrating the overhead aqueous ethanol stream in a distillation column to provide ethanol;
   wherein the ethanol-containing biomass mixture in step (a) has a viscosity of at least 500 cP.

2. The process according to claim 1, wherein the overhead aqueous ethanol streams fed to the distillation column in step (f) have a combined initial ethanol concentration of about 20% by weight.

3. The process according to claim 1, wherein ethanol-containing biomass mixture is derived from a biomass feedstock comprising citrus waste.

4. The process according to claim 1, wherein step (c) is carried out in a flash vaporization unit.

5. The process according to claim 4, wherein steam is introduced into the vaporization unit to assist in a stripping of ethanol.

6. The process according to claim 1, wherein a vacuum system is employed to assist a separation of ethanol in at least one of steps (c), (d), and (e).

7. The process according to claim 1, wherein the overhead aqueous ethanol stream from step (f) is utilized as the overhead aqueous ethanol steam for a previous separation stage.

8. The process according to claim 1, wherein the ethanol-containing biomass mixture of step (a) has a viscosity of from at least 500 to about 20000 cP.

9. The process according to claim 8, wherein the ethanol-containing biomass mixture of step (a) has a viscosity of from at least 1000 to about 10000 cP.

10. The process according to claim 1, wherein the distillation column in step (e) is a stripping column packed with distillation trays suitable for a biomass feedstock.

11. The process according to claim 1, further comprising:
    heating the ethanol-containing biomass mixture prior to separating the ethanol-containing biomass mixture.

* * * * *